(12) United States Patent
Sawada et al.

(10) Patent No.: US 6,713,252 B2
(45) Date of Patent: Mar. 30, 2004

(54) METHOD FOR REMOVING AND REDUCING HEPATITIS C VIRUS

(75) Inventors: Kouji Sawada, Kashiba (JP); Takashi Shimoyama, Kobe (JP)

(73) Assignee: Japan Immunoresearch Laboratories Co., Ltd., Gunma (JP)

( * ) Notice: Subject to any disclaimer, the term of this patent is extended or adjusted under 35 U.S.C. 154(b) by 0 days.

(21) Appl. No.: 10/180,098

(22) Filed: Jun. 27, 2002

(65) Prior Publication Data

US 2003/0152569 A1 Aug. 14, 2003

(30) Foreign Application Priority Data

Feb. 14, 2002 (JP) ........................ 2002-037279

(51) Int. Cl.$^7$ .................... C12Q 1/70; A61K 38/21; A61M 1/38
(52) U.S. Cl. .................. 435/5; 435/7.24; 424/140.1; 424/85.4; 604/5.02; 604/6.03; 436/518
(58) Field of Search ................ 424/140.1, 85.4; 604/5.02, 6.03; 435/5, 7.21; 436/518

(56) References Cited

U.S. PATENT DOCUMENTS

| | | |
|---|---|---|
| 5,567,443 A | 10/1996 | Kashiwagi et al. |
| 5,725,768 A | 3/1998 | Adachi et al. |
| 6,498,007 B1 * | 12/2002 | Adachi et al. ................ 435/5 |

FOREIGN PATENT DOCUMENTS

| | | |
|---|---|---|
| EP | 0319961A2 A3 | 6/1989 |
| EP | 0 972 530 A1 * | 1/2000 |
| WO | WO 00/55621 | 9/2000 |

OTHER PUBLICATIONS

Kuramochi et al, *J. Artif. Organs,* 4:146–149 (2001).
The 66–th Japanese Society for Interferon and Cytokine Research, Chairman: Haruki Okamura (Institute for Advanced Medical Sciences / Hygo College of Medicine), Dates Jul. 13–14, 2001, International Conference Center Kobe (Port Island), Abstract B8.

* cited by examiner

*Primary Examiner*—Donna C. Wortman
(74) *Attorney, Agent, or Firm*—Sughrue Mion, PLLC

(57) ABSTRACT

Described is a method of removing and reducing HCV from the blood of an HCV-infected patient, which comprises carrying out, once a day for at least 5 straight days, a treatment of bringing the blood into contact with an adsorptive carrier having a higher affinity for infected, activated and/or defective leukocytes than for uninfected leukocytes. The treatment according to the present invention makes it possible to markedly reduce the blood HCV level of a patient suffering from Hepatitis C, thereby enabling antiviral therapy, for example, treatment with interferon. This brings a drastic improvement in the cure rate for Hepatitis C.

12 Claims, 5 Drawing Sheets

METHOD FOR REMOVING AND REDUCING HEPATITIS C VIRUS

BACKGROUND OF THE INVENTION

1. Field of the Invention

The present invention relates to a method for removing and reducing Hepatitis C virus (HCV) in the blood of patients infected with HCV; and a method for treating HCV infectious diseases.

2. Description of the Related Art

Hepatitis C is a viral infection of the liver having a high risk of progressing to cirrhosis or liver cancer. After HCV, which is causative of Hepatitis C, infects cells, for example liver cells, it harbors in these cells and leukocytes during the incubation period.

Apheresis has recently been employed for the purpose of treating various diseases.

In EP-A-0-319961, there is described a method of selectively removing granulocytes from blood by bringing the blood into contact with an adsorptive carrier having a higher affinity for granulocytes than for lymphocytes. That invention is concerned with cancer treatment. An apparatus for carrying out the method is also described in that application. A similar apparatus is described in U.S. Pat. No. 5,725,768.

In U.S. Pat. No. 5,567,443, there is described a method of treating inflammatory diseases which comprises bringing the blood of a patient into contact with an adsorptive carrier having a higher affinity for inflammatory cells (granulocytes and monocytes) than for lymphocytes. The method is reported to be useful for treating acute respiratory distress syndrome, rheumatoid arthritis, autoimmune diseases, allergic diseases and reflow disorders following myocardial infarction.

With the foregoing in view, the present inventors found a method of removing, from the blood containing leukocytes infected with HIV, HCV and/or the like virus and thereby activated and/or defective, the infected leukocytes by bringing the blood into contact with an adsorptive carrier having a higher affinity for the infected, activated and/or defective leukocytes than for uninfected, non-activated and/or non-defective leukocytes and applied for a patent for it (WO00/55621).

According to the typical method disclosed therein, the blood is brought into contact with the adsorptive carrier once a week. There is a demand for the development of a more effective method for removing and reducing HCV based on the above-described method.

SUMMARY OF THE INVENTION

The present inventors have carried out various investigations on the method of using apheresis for effectively removing and reducing HCV from the blood. As a result, it has been found that HCV can be removed and reduced from the blood very smoothly and effectively by conducting apheresis treatment once a day for at least 5 straight days, and this treatment brings about a marked improvement in the therapeutic effects of interferon or the like, leading to the completion of the present invention.

In one aspect of the present invention, there is thus provided a method of removing and reducing HCV from the blood of a patient infected with HCV by bringing the blood into contact with an adsorptive carrier having a higher affinity for infected, activated and/or defective leukocytes than for uninfected leukocytes once a day for 5 straight days.

In another aspect of the present invention, there is also provided a method of treating HCV infection, which comprises bringing the blood of a patient infected with HCV into contact with an adsorptive carrier having a higher affinity for infected, activated and/or defective leukocytes than for uninfected leukocytes once a day for 5 straight days, and then administering an interferon to the patient.

The treatment according to the present invention makes it possible to markedly reduce the blood HCV level of a patient suffering from Hepatitis C and therefore enables antiviral therapy, for example, therapy with interferon. It therefore contributes to a drastic improvement in the cure rate of Hepatitis C.

DETAILED DESCRIPTION OF THE PREFERRED EMBODIMENTS

Figure 1:
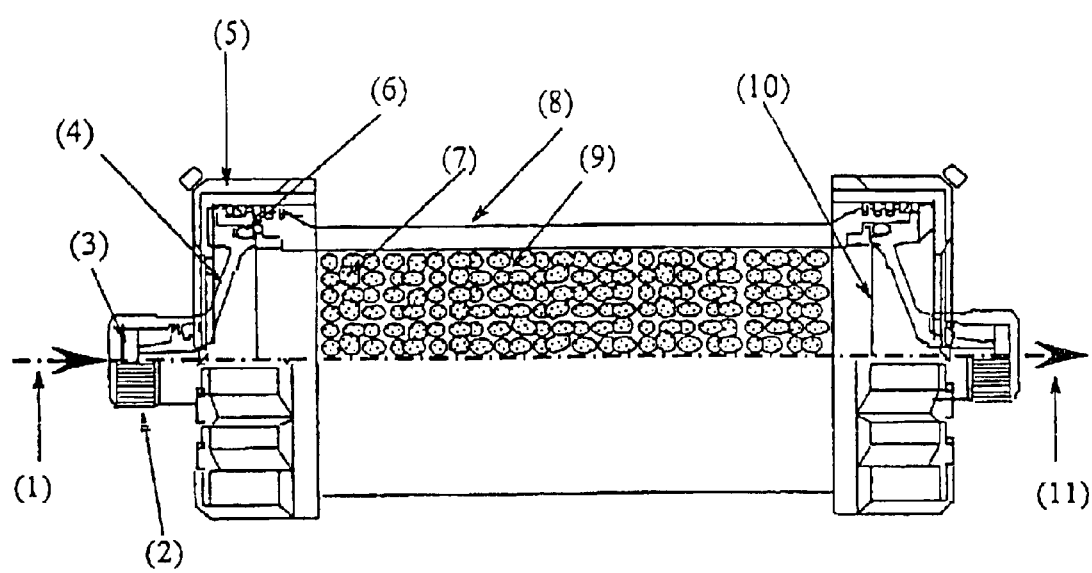
FIG. 1 schematically illustrates the constitution of of a leukocyte apheresis column according to one embodiment of the invention.

The term "adsorptive carrier" as used herein means a material capable of adsorbing, to the surface thereof, cells.

The adsorptive carrier usable in the present invention has higher affinity for HCV-infected, activated and/or defective leukocytes than for HCV-uninfected, non-activated and/or non-defective leukocytes and does not adversely affect the blood brought into contact with the adsorbent.

The efficiency of a specific cell type to be adsorbed to a particular adsorptive carrier is calculated in accordance with the following equation:

$$\text{Trapping efficiency (\%)} = \frac{\text{The number of cells adsorbed}}{\text{The number of cells exposed to adsorptive carrier}} \times 100$$

Differential leukocyte count (the number of a specific leukocyte type) is determined by a standard-laboratory-size differential leukocyte counter, for example, "THMS H-1" (Technicon). The count of specific leukocyte type cells trapped by the carrier in the column is calculated by subtracting, from the corresponding leukocyte count in the blood at the column inlet, the appropriate leukocyte count in the blood at the column outlet. The count of the cells exposed to the carrier is calculated from the flow rate (mL/min), flow time (apheresis time) and the appropriate leukocyte count at the inflow.

The adsorptive carrier to be used in the present invention is preferably a carrier having an affinity for HCV, particularly a carrier having a high affinity for the blood HCV bonded to proteins, lipids or immune complexes. Moreover, the adsorptive carrier is preferably a carrier having complement activating action. The term "complement activating action" as used herein embraces the action via the classical pathway and that via the alternative pathway. The complement activation is confirmed by measuring C3a, C3b, C5a and C5b produced by the activation. In the present invention, a carrier capable of activating complement by about 2 to 100 times is preferred and use of such a carrier makes it possible to remove and reduce HCV efficiently.

As the adsorptive carrier usable in the present invention, that having a contact angle to water in a range of from 55° to 95° is preferred.

The term "contact angle" as used herein means an angle made by a free surface of a stationary liquid and a solid surface at a point where the free surface is in contact with the solid surface. The angle located inside the liquid is employed. Contact angles of principal adsorptive carriers to water are shown in Table 1.

TABLE 1

| Material | Contact angle to water (°) |
| --- | --- |
| Cellulose acetate | 60 |
| Polystyrene | 91 |
| Nylon | 70 |
| Polytetrafluoroethylene (TEFLON) (Reference Compound) | 108 |
| Polytrifluoroethylene | 92 |
| Polyethylene terephthalate | 81 |
| Polyethylene | 94 |
| Polyvinyl chloride | 87 |
| Polyvinyl alcohol (Reference compound) | 36 |
| Acrylic resin (Reference compound) | 54 |
| Glass (Reference compound) | 8 |
| Ethyl cellulose | 64 |

Adsorbent carriers having a contact angle within a range of 55 to 95°, for example, those described in Table 1 are suited for adsorption of HCV-infected, activated and/or defective leukocytes including mononuclear cells (monocytes/macrophages), neutrophils and $CD4^+$ lymphocytes. Through these carriers, activated leukocytes including mononuclear cells (monocytes/macrophages), neutrophils and $CD4^+$ lymphocytes can be removed effectively from the blood. Moreover, adsorption of other blood cell components, plasma components and serum components may be suppressed to the minimum. Two or more adsorptive carriers may be used in combination.

Particularly suited examples of the adsorptive carrier in the present invention include polystyrene, cellulose acetate, nylon such as 6-nylon and 11-Nylon, polytrifluoroethylene and polyethylene terephthalate. Of these, cellulose acetate is a more preferred adsorptive carrier.

Although no particular limitation is imposed on the shape and size of the adsorptive carrier, preferred is the adsorptive carrier which has a size large enough to be distinguished from blood cells and has a shape having a large contact area with the blood to be brought into contact therewith, in order to permit effective contact. For example, the adsorptive carrier may take the form of beads having a diameter of about 0.1 to 10 mm. These beads preferably have a diameter ranging from 0.2 to 5.0 mm, more preferably from 0.5 to 4.0 mm, especially 1.0 to 3.0 mm, for example, 2.0 mm.

The rougher the surface of the adsorptive carrier, its HCV removing and reducing efficiency increases. The adsorptive carrier having, on the surface thereof, surface roughness having a centerline average height Ra, as defined under Japanese Industrial Standards B0601-1982, of 0.2 to 10 μm and a mean spacing Sm of unevenness within a range of 5 to 200 μm is particularly preferred. The effectiveness of an apheresis adsorptive carrier having such surface characteristics is described in U.S. Pat. No. 5,593,586 and a preparation process of such an adsorptive carrier is described in U.S. Pat. No. 5,525,279.

Cellulose acetate is especially preferred as a material for the adsorptive carrier. Cellulose acetate adsorptive carriers in the form of beads having a diameter of about 0.1 to 10 mm, preferably 0.2 to 5.0 mm, more preferably 0.5 to 4.0 mm, still more preferably 1.0 to 3.0 mm, especially 2.0 mm are preferred.

The rougher the surface of the cellulose acetate adsorptive carrier, the removing and reducing efficiency of HCV thereby increases. The efficiency is enhanced particularly when the adsorptive carrier has a roughened surface as described above.

In the present invention, contacting treatment of the blood with the adsorptive carrier once a day for at least 5 straight days makes it possible to efficiently remove and remove HCV from the blood of a patient infected with HCV. The conventional treatment conducted once a week cannot remove and reduce HCV sufficiently. Treatment once a day for 5 to 15 straight days is more preferred.

In the present invention, the blood is treated preferably in an amount of 300 to 3000 mL/once, particularly about 2000 mL/once. Such an amount is attained by the treatment of the blood at a rate of 5 to 200 mL/min for 10 minutes to 10 hours, especially, at a rate of 20 to 50 mL/min for about 1 hour.

By the above-described treatment, the blood HCV level can be reduced to an amount small enough to be susceptible upon antiviral therapy by interferon or the like. As such an amount, the blood HCV level, as measured by the RT-PCR method, less than 100 KIU/mL is preferred.

In the present invention, the plasma, separated from other blood components, may be brought into contact with the above-described adsorptive carrier. As described above, it is preferred to return the blood or plasma thus treated to the body from which it is taken out.

The leukocyte apheresis apparatus to be used in the present invention has a means for bringing blood containing infected, activated and/or defective leukocytes into contact with the adsorptive carrier and then recovering the thus-treated blood. The blood of a patient to be treated is preferably peripheral blood. The above-described device may further have a transporting means for returning the treated blood to the patient. One or both of the transporting means may have a pumping means. One or both of the transporting means may have a means for measuring the flow rate and/or pressure of the blood within the transporting means. In some cases, a means for adding a medicament to the blood may be present in one or both of the transporting means.

A leukocyte apheresis column to be used in the present invention is filled with an adsorptive carrier immersed in a physiological liquid, particularly in sterilized physiological saline. The adsorptive carrier in the form of beads is especially preferred. The blood is fed to the column through a blood inlet and then, discharged from a blood outlet. The blood inlet is sometimes connected to a proper blood vessel of a patient, for example, a blood vessel in an arm or a hand via a transporting means, for example, a tube. Similarly, the blood outlet may be connected to another proper blood vessel of the patient, for example, a blood vessel of an arm or a hand.

If HCV in the blood of a patient can be removed and reduced to a sufficiently low level according to the present invention, an antiviral therapy conducted subsequent thereto for the patient by using interferon or the like will heighten the cure rate for HCV infection. Any kind of interferon is usable here and it can be administered in accordance with the ordinary dosage and administration. During antiviral therapy by using interferon, it is not necessary to terminate the contact treatment of the blood with the adsorptive carrier of the present invention. The invention treatment not everyday but, for example, once a week is sufficient during antiviral therapy by using interferon.

A leukocyte apheresis apparatus according to one embodiment of the present invention will next be described based on FIG. 1 and FIG. 2 of the accompanying drawings.

Leukocyte Apheresis Column

The column is filled with cellulose acetate beads (adsorptive carrier) of 2 mm diameter immersed in sterilized physiological saline. The blood is ordinarily drawn and returned via suitable cubital veins in the left and right hands. This system has been developed for selective adsorption of activated or HCV-infected leukocytes including monocytes/macrophage and neutrophils and HCV.

Constitution of G-1 Column Leukocyte Apheresis Apparatus

The structure of G-1 Column (Adacolumn) manufactured in accordance with the present invention is shown in FIG. 1, while the material constituting the column is described in Table 1. FIG. 2 is a schematic view of the G-1 Column leukocyte apheresis apparatus.

As illustrated in FIG. 1, G-1 column (Adacolumn) is a column (8) made of polycarbonate and, filled therein, cellulose acetate beads (adsorptive carrier (7)) immersed in sterilized physiological saline (9). The column contents are hermetically sealed with an inner cap (4), outer cap (5) and O-ring (6). A blood feed line is attached to the column at a blood inlet (1) with a nozzle cap (2) and packing (3). The adsorptive carrier beads have a diameter of 2 mm and have a total weight of 220 g. The column has a length of 206 mm, diameter of 60 mm and capacity of 335 mL. The total volume of the physiological saline is 130 mL (equal to the column void volume).

The constituents of the G-1 column (Adacolumn) are shown in Table 2.

TABLE 2

| Name | Raw material |
|---|---|
| Adsorptive carrier* | Cellulose acetate |
| Main body* | Polycarbonate |
| Outer cap* | Polypropylene |
| Inner cap* | Polypropylene |
| O-ring* | Silicone rubber |
| Perforated stopper* | Polyethylene terephthalate |
| Packing | Silicone rubber |
| Nozzle cap | Polypropylene |
| Solution to be filled | Isotonic physiological saline |
| Circuit line | PVC (polyvinyl chloride, plasticized) |
| Package film | Nylon/polypropylene laminate film, partially gas-permeable wood-free paper or nonwoven fabric (nylon/C.P.P. film) |

*means that the constituent comes into direct contact with the blood.

Figure 2:
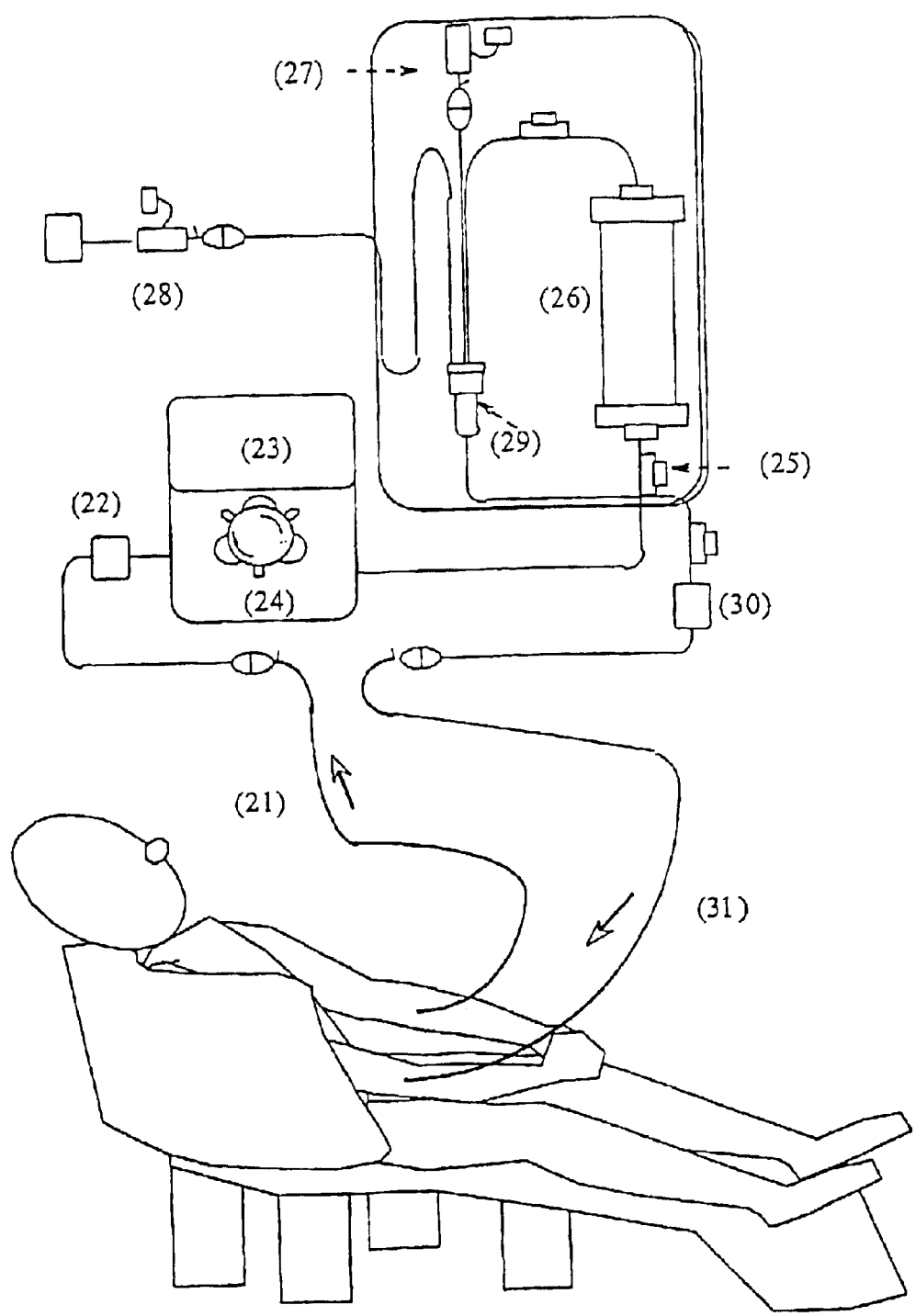
FIG. 2 illustrates the components of a leukocyte apheresis device according to one embodiment of the invention.

As illustrated in FIG. 2, the G-1 leukocyte apheresis apparatus is made of G-1 column (Adacolumn (26)), blood circuit line and Adamonitor. Blood from the antecubital vein of a patient (21) is drawn into the pump (24) and Adamonitor (23), passing through a bubble detector (22). Then, the blood passes an anticoagulant administration port (25) before entering Adacolumn (26). After outflow from the column, the blood flows into a drip chamber (29). The drip chamber is equipped with a drip chamber air outlet (27) and a venous pressure gauge (28). The blood then passes through a bubble detector (30) and is then returned to the patient via an antecubital vein (31).

EXAMPLES

The present invention will hereinafter be described in further detail by Examples. It should however be borne in mind that the present invention is not limited to or by them.

Example 1

Three patients suffering from chronic Hepatitis C were subjected to apheresis once a day for 5 straight days by using G-1 Column having the constitution as shown in FIGS. 1 and 2, and Table 2 and variations in their blood HCV levels were measured. They were then administered with interferon to treat hepatitis.

(1) Apheresis Conditions

After each patient was subjected to apheresis once a day for 5 straight days, the blood HCV level was measured. If it was judged to fall within a range permitting interferon therapy (less than 100 KIU/mL), interferon therapy was conducted. Apheresis was conducted continuously for 60 minutes at a flow rate of 30 mL/min. During the treatment, the serum AST (GOT) and ALT (GPT), indicators of hepatitis, were measured. The blood HCV level was measured by the RT-PCR method ("AMPLICOR GT HCV Monitor V2.0", trade name; manufactured by Roche Diagnostics Corporation).

(2) Results

Figure 3:
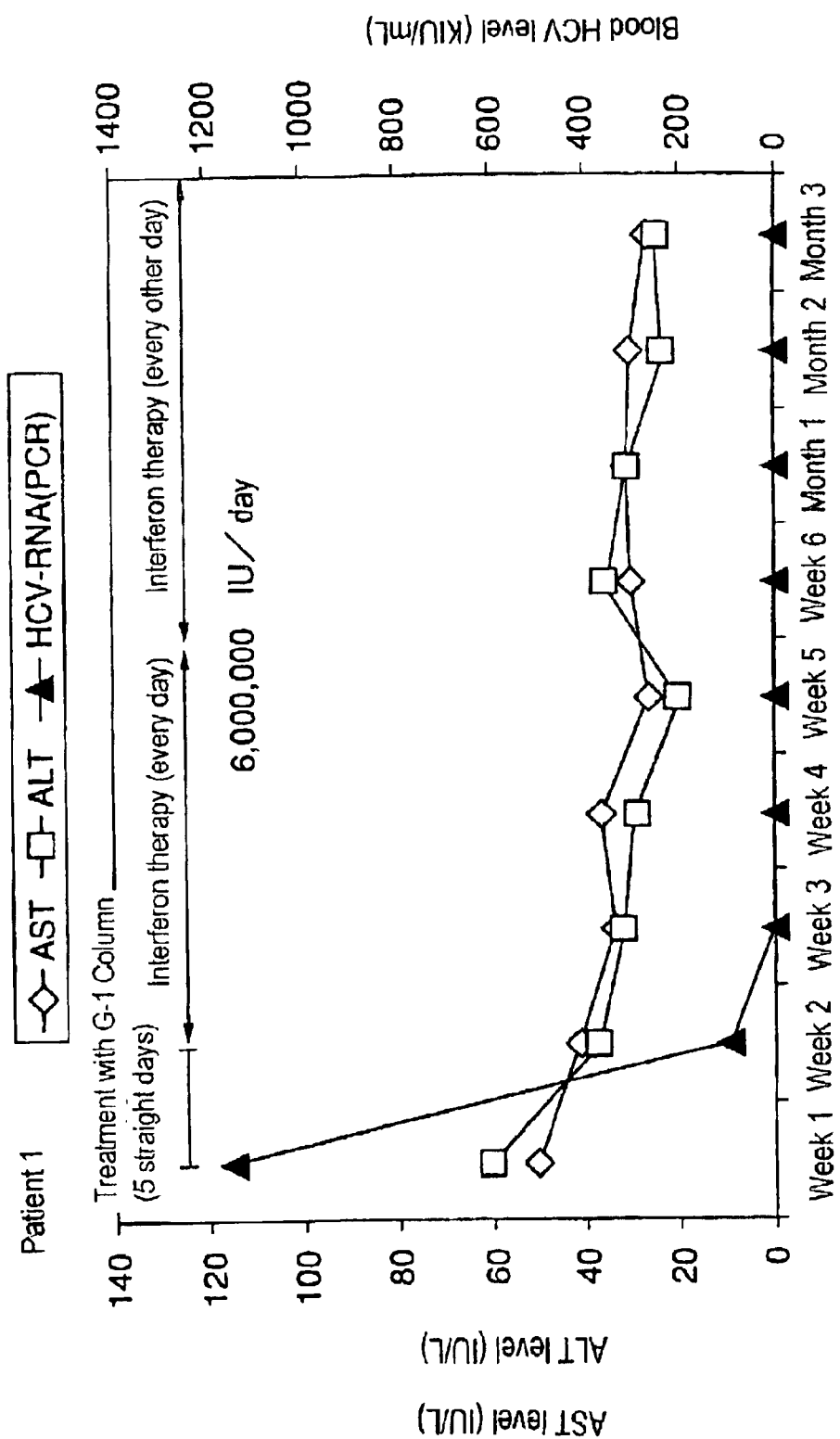
FIGS. 3 to 5 are graphs each showing variations in HCV, AST and ALT levels, during apheresis treatment, of three patients suffering from Hepatitis C and therefore having a high blood HCV level before apheresis.
Figure 4:
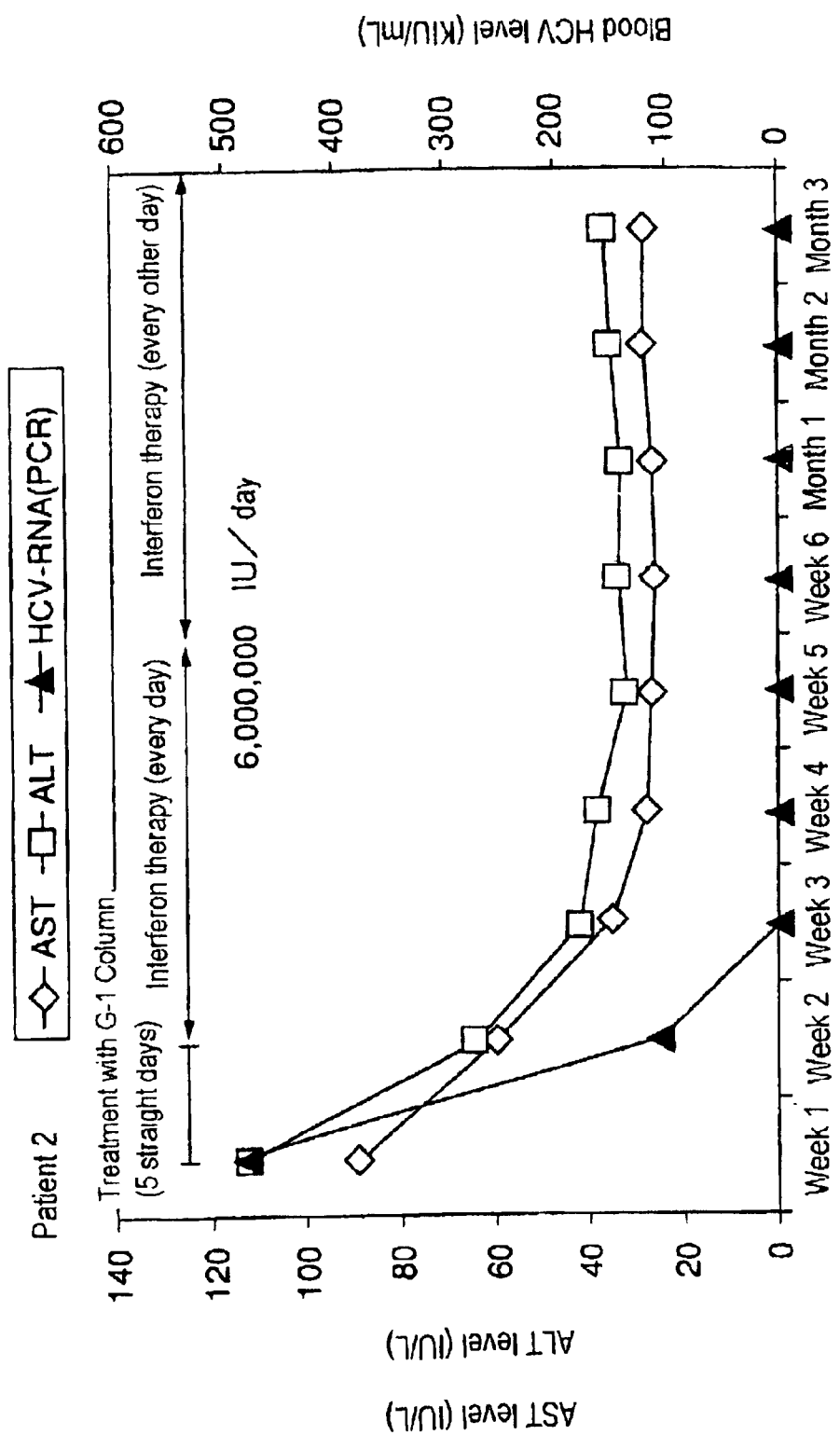
Figure 5:
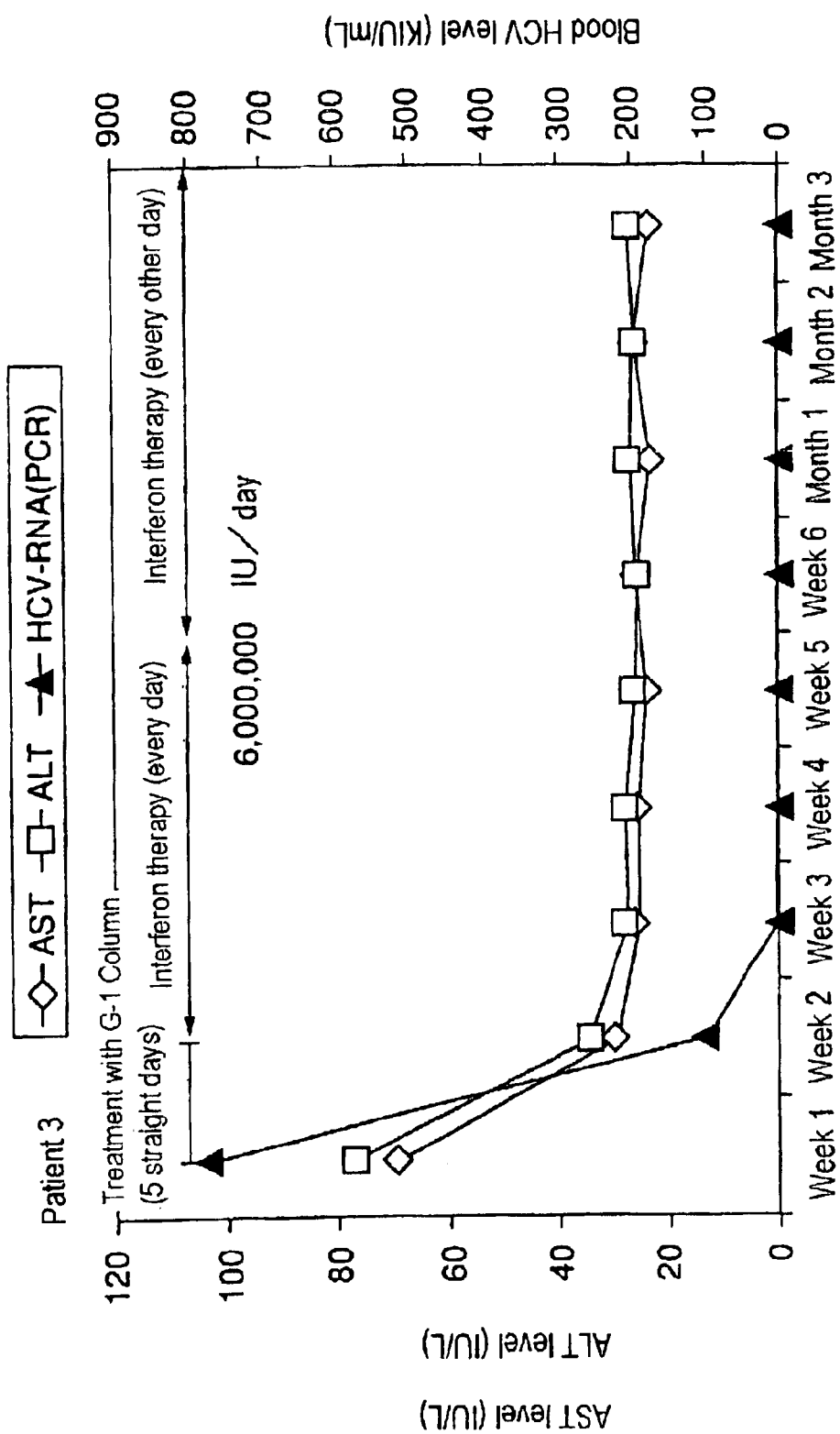

The results are shown in FIGS. 3 to 5. As apparent from the results shown in FIGS. 3 to 5, each patient exhibited a high HCV level exceeding 500 KIU/mL before the treatment of the present invention (average HCV level of three patients before treatment: 806 KIU/mL), which, however, reduced to 100 KIU/mL or less after the treatment of the present invention once a day for 5 straight days. Such a low HCV level enabled interferon therapy. Five days later, interferon therapy for these three patients was started, resulting in substantial disappearance of HCV from the blood for 3 months. It is to be noted that the interferon administered to them was similar in kind to the interferon which had been once administered to them and proved to be ineffective. The effect of the present invention was therefore confirmed.

What is claimed is:

1. A method for removing and reducing HCV from the blood of an HCV-infected patient, which comprises carrying out, once a day for at least 5 straight days, a treatment of bringing the blood into contact with an adsorptive carrier having a higher affinity for infected, activated and/or defective leukocytes than for uninfected leukocytes.

2. The method of claim 1, wherein the adsorptive carrier additionally has an affinity for HCV.

3. The method of claim 2, wherein the blood is separated into plasma and other components and the plasma is brought into contact with the adsorptive carrier.

4. The method of claim 3, wherein the plasma after treatment is returned to the body from which it is taken out.

5. The method of claim 1, wherein the adsorptive carrier has complement activating action.

6. The method of claim 1, wherein the adsorptive carrier has a contact angle to water within a range of from 55 to 95°.

7. The method of claim 1, wherein the treatment of bringing the blood into contact with the adsorptive carrier is conducted once a day for 5 to 15 straight days.

8. The method of claim 1, wherein the blood is treated in an amount of 300 to 3000 mL/once.

9. The method of claim 1, wherein one treatment of bringing the blood into contact with the adsorptive carrier is conducted for 10 minutes to 10 hours at a rate of 5 to 200 mL/min.

10. The method of claim 1, wherein the blood after treatment is returned to the body from which it is taken out.

11. The method of claim 1, wherein the treatment of bringing the blood into contact with the adsorptive carrier is continued until the blood HCV level, as measured by the RT-PCR method, becomes below 100 KIU/mL.

12. A method of treating HCV infection, which comprises carrying out, once a day for at least 5 straight days, a treatment of bringing the blood of an HCV-infected patient into contact with an adsorptive carrier having a higher affinity for infected, activated and/or defective leukocytes than for uninfected leukocytes and then administering interferon to the patient.

* * * * *